(12) United States Patent
Benchikh et al.

(10) Patent No.: US 9,784,752 B2
(45) Date of Patent: Oct. 10, 2017

(54) VENLAFAXINE ASSAY

(71) Applicant: Randox Laboratories, Limited, Crumlin, Antrim (GB)

(72) Inventors: Elouard Benchikh, Antrim (GB); Ivan McConnell, Antrim (GB); Philip Lowry, Antrim (GB); Peter Fitzgerald, Antrim (GB)

(73) Assignee: Randox Laboratories Limited, Crumlin, Antrim (GB)

( * ) Notice: Subject to any disclaimer, the term of this patent is extended or adjusted under 35 U.S.C. 154(b) by 496 days.

(21) Appl. No.: 13/861,093

(22) Filed: Apr. 11, 2013

(65) Prior Publication Data

US 2014/0147859 A1    May 29, 2014

(30) Foreign Application Priority Data

Apr. 11, 2012 (GB) .................... 1206398.8

(51) Int. Cl.
*G01N 33/94* (2006.01)
*C07C 217/64* (2006.01)

(52) U.S. Cl.
CPC ....... *G01N 33/9466* (2013.01); *C07C 217/64* (2013.01)

(58) Field of Classification Search
CPC .......................... C07C 217/64; G01N 33/9466
See application file for complete search history.

(56) References Cited

U.S. PATENT DOCUMENTS

| 6,991,911 B2 * | 1/2006 | Zheng | C07D 317/58 |
| | | | 424/175.1 |
| 2004/0147601 A1 * | 7/2004 | Yardley | C07C 217/64 |
| | | | 514/546 |
| 2006/0223132 A1 * | 10/2006 | McConnell | C07K 16/44 |
| | | | 435/7.92 |

OTHER PUBLICATIONS

Sena et al., "False-Positive Phencyclidine Immunoassay Results Caused by Venlafaxine and O-Desmethylvenlafaxine," Clin. Chem., 2002, vol. 48, No. 4, pp. 676-677.*
A print-out retrieved from http://webserver.pa-ucl.com/wwwdocs/analyticalproc/FrameA.htm on Sep. 23, 2015.*
Bhatt et al., "Liquid chromatography-tandem mass spectrometry (LC-MS-MS) method for simultaneous determination of venlafaxine and its active metabolite O-desmethyl venlafaxine in human plasma," J. Chromatography B, 2005, vol. 829, issues 1-2, pp. 75-81.*
Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Englebienne, "Immune and Receptor Assays in Theory and Practice," CRC Press, 2000, p. 308.*
Manchikanti et al., "Protocol for accuracy of point of care (POC) or in-office urine drug testing (immunoassay) in chronic pain patients: a prospective analysis of immunoassay and liquid chromatography tandem mass spectometry (LC/MS/MS)," Pain Physician., Jan.-Feb. 2010;13(1):E1-E22.*
Brandhorst et al., "Liquid chromatography-tandem mass spectrometry or automated immunoassays: what are the future trends in therapeutic drug monitoring?" Clin. Chem. 2012, vol. 58, No. 5, pp. 821-825; doi: 10.1373/clinchem.2011.167189; Epub Jan. 17, 2012.*
Allen, K.R., (2006) "Interference by Venlafaxine Ingestion in the Detection of Tramadol by Liquid Chromatography Linked to Tandem Mass Spectrometry for the Screening of Illicit Drugs in Human Urine," Clin. Toxicol., vol. 44: pp. 147-53.
Daughton, C.G. and Brooks, B.W., (2011) "Environmental Contaminants in Biota: Interpreting Tissue Concentrations," Chapter 8, pp. 286-347, W. Nelson Beyer and James P. Meador (Eds.), 2nd ed., CRC Press, Taylor & Francis Group, Boca Raton, FL.
Fitzgerald, S.P. et al., (2005) "Development of a High-Throughput Automated Analyzer Using Biochip Array Technology," Clin. Chem., vol. 51(7): pp. 1165-76.
European Search Report, Application No. EP13163144, dated Jun. 21, 2013.
Qin et al., "Determination of venlafaxine in human plasma by high-performance liquid chromatography using cloud-point extraction and spectrofluorimetric detection", The Journal of Chromatography B: Analytical Technologies in the Biomedical and Life Sciences, 2008, vol. 872, Issue 1-2, pp. 38-42, Abstract only.
Salvador et al., "False-Positive Phencyclidine Immunoassay Results Caused by Venlafaxine and O-Desmethylvenlafaxine" Clinical Chemistry, 2002, vol. 48, No. 4, pp. 676-677.

* cited by examiner

*Primary Examiner* — Galina Yakovleva
(74) *Attorney, Agent, or Firm* — MacMillan, Sobanski & Todd, LLC (57) ABSTRACT

The invention describes antibodies that bind venlafaxine and O-desmethylvenlafaxine. The antibodies are derived from novel haptens and immunogens and are used in methods and kits to detect and quantify venlafaxine and O-desmethylvenlafaxine. The invention also describes novel detecting agents which can be used in the methods and kits of the invention.

1 Claim, 4 Drawing Sheets

VENLAFAXINE ASSAY

CROSS-REFERENCE TO RELATED APPLICATIONS

This application claims the benefit of priority to U.K. Application No. 1206398.8 filed Apr. 11, 2012, the disclosure of which is incorporated herein by reference.

BACKGROUND TO THE INVENTION

The invention relates to the field of analytical clinical chemistry and environmental residue monitoring and the detection and quantification of the antidepressant drug venlafaxine (IUPAC name: (RS)-1-[2-dimethylamino-1-(4-methoxyphenyl)ethyl]cyclohexanol). Introduced in the early 1990s, it belongs to drugs of the serotonin noradrenergic reuptake inhibitor class and is metabolized by the cytochrome P enzyme CYP2D6 to its major (and active) metabolite O-desmethylvenlafaxine (IUPAC name: (RS)-1-[2-dimethylamino-1-(4-hydroxyphenyl)ethyl]-cyclohexanol). There are clinical requirements for the detection, following drug overdose and for therapeutic drug monitoring, of both the parent drug and its main metabolite. There is also a need for their non-clinical detection, with venlafaxine being amongst the increasing number of pharmaceuticals detected in the environment (Daughton and Brooks 2010).

Current analytical methods use mass-spectrometry (MS) in conjunction with gas chromatography (GC) or liquid chromatography (LC). These methods are resource intensive, requiring expensive equipment and highly trained staff for their operation. Furthermore, use of these methods for the confirmation of venlafaxine use can be subject to uncertainty. Tramadol and O-desmethyl-venlafaxine were shown to have similar retention indices and overlapping fragmentation ions, leading to difficulties and uncertainty with the identification of tramadol in the presence of venlafaxine using a LC-MS-MS system (Allen 2006). In light of the current state of the art, what is required is a simplistic and economical detection method that is able to specifically detect venlafaxine and O-desmethylvenlafaxine.

SUMMARY OF THE INVENTION

Immunoassays represent a relatively simplistic and economical alternative to established analytical methods for use in toxicology, therapeutic drug monitoring (TDM) and environmental residue monitoring. The invention described herein is intended to circumvent at least some of the previously-mentioned problems associated with current methodologies used for venlafaxine analysis and provides the first known immunoassay for the detection of venlafaxine and its major metabolite O-desmethylvenlafaxine. The immunoassay is based on antibodies with specific binding properties, derived from novel haptens and immunogens. Also described are novel detection agents, methods, kits, and uses.

DETAILED DESCRIPTION

Figure 1:
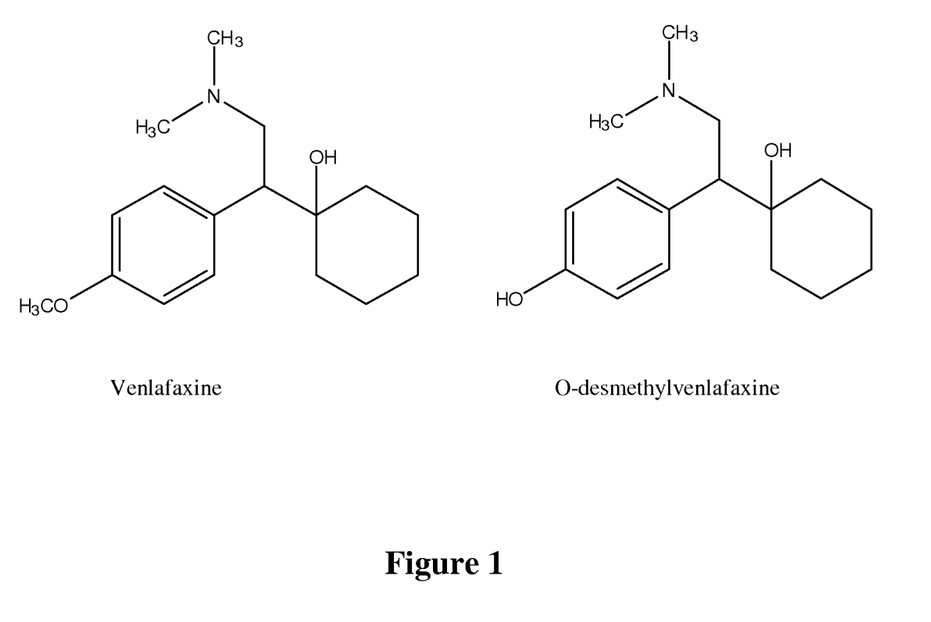
FIG. 1 Structures of venlafaxine and O-desmethylvenlafaxine
Figure 2:
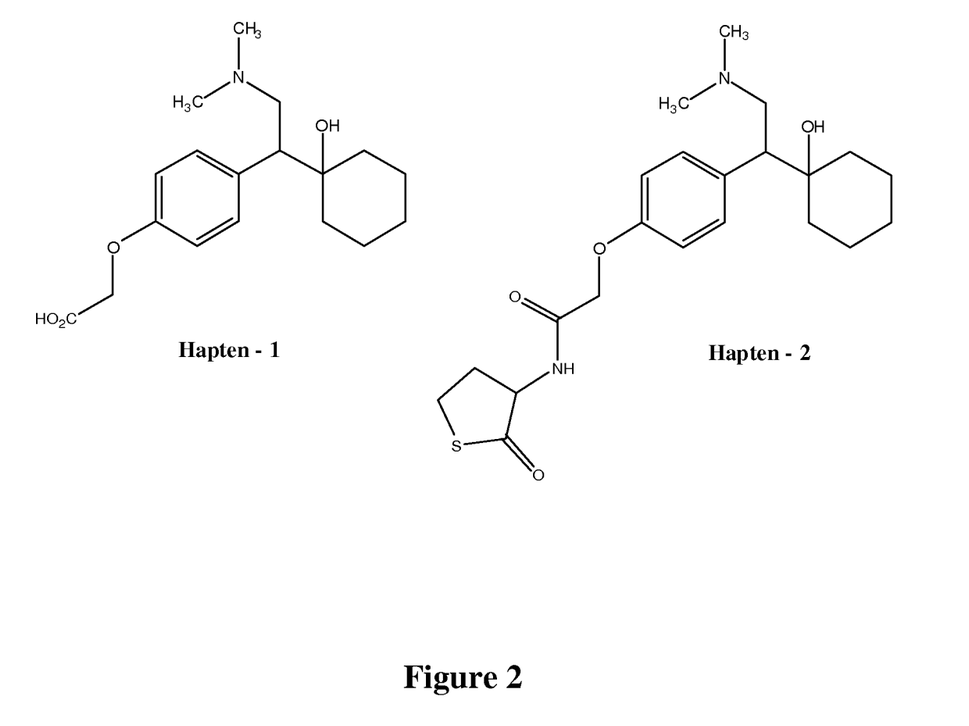
FIG. 2 Haptens 1 and 2
Figure 3:
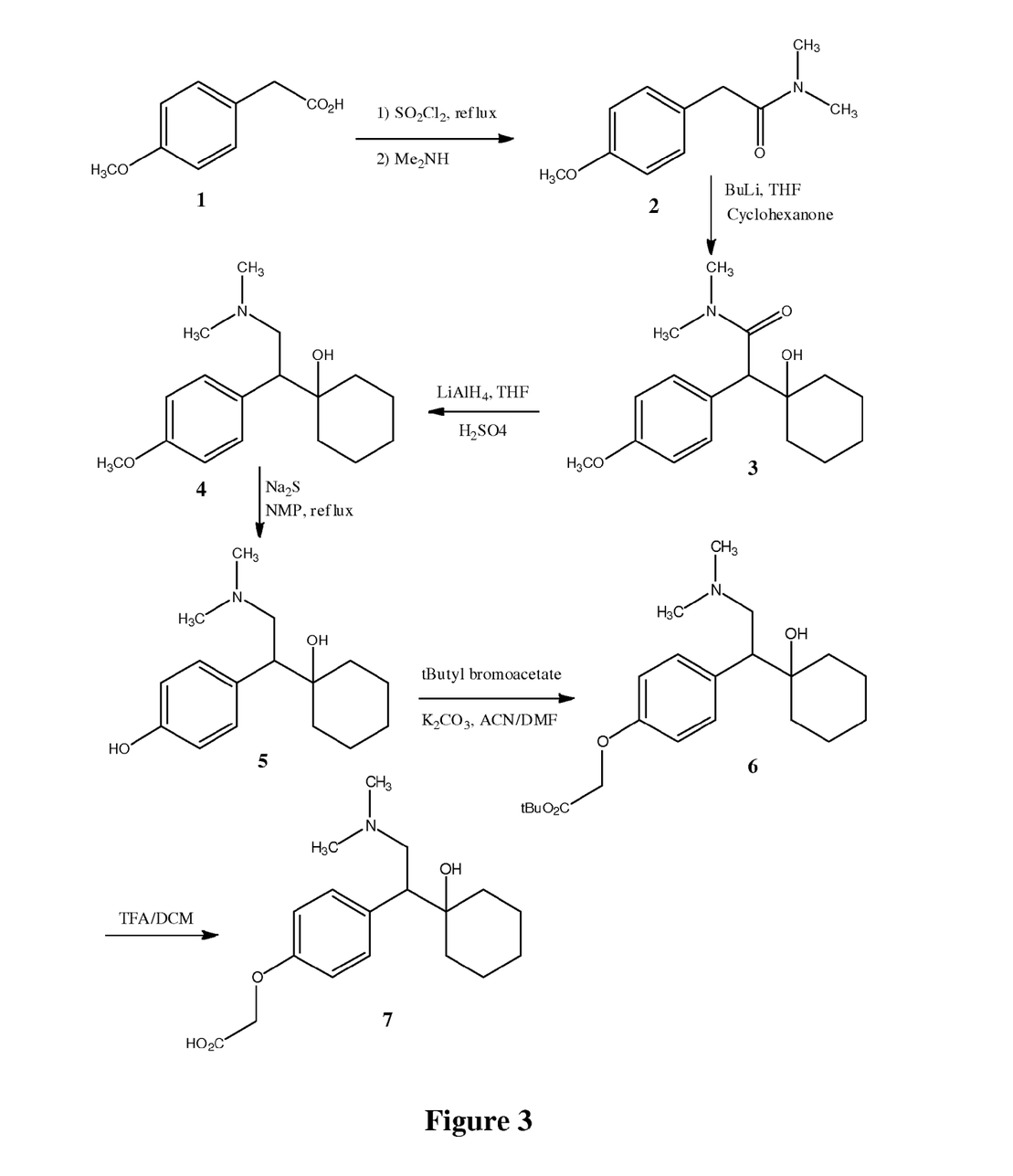
FIG. 3 Synthetic route to Hapten 1
Figure 4:
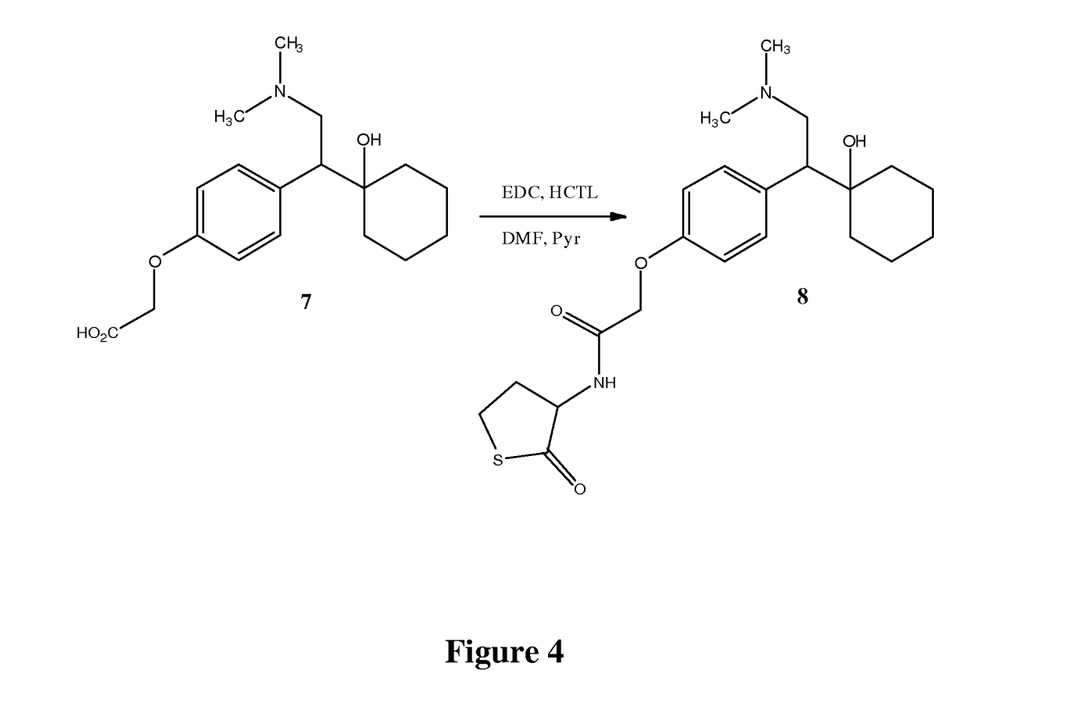
FIG. 4 Synthetic route to Hapten 2

In a first aspect, the invention describes haptens, detecting agents, and immunogens of Formula I:

wherein
R(a-R-b) is selected from the group consisting of:

and wherein

X is selected from the group consisting of N, O, and S; n=0 or 1;

Y is a substituted or unsubstituted $C_1$-$C_{10}$, more preferably a $C_1$-$C_6$, most preferably a $C_1$-$C_3$, branched or straight chain alkylene moiety;

for the hapten, Z is selected from the group consisting of a carboxyl, dithiopyridyl, maleimidyl, amino, hydroxyl, thiol, and aldehyde moiety;

for the detecting agent and immunogen Z is -(A)-B, in which B for the detecting agent is selected from the group consisting of an enzyme, luminescent substance, and a radioactive label and for the immunogen B is an antigenicity-conferring carrier material (accm) and A, before connection to the detectable labelling agent or antigenicity conferring carrier material, is selected from the group consisting of a carboxyl, dithiopyridyl, maleimidyl, amino, hydroxyl, thiol, and an aldehyde moiety.

For the avoidance of doubt, the ring incorporating R is an aromatic benzene ring (phenyl moiety), which, in the context of Formula I, would be named a meta or para substituted phenylene ring by the International Union of Pure and Applied Chemistry (IUPAC). In a preferred embodiment the —(X)$_n$—Y—Z substituent is at the para position of the aromatic ring. Preferably, for the hapten n=1, X is O, Y is —CH$_2$—, and Z is carboxy. Preferably, for the detecting agent n=1, X is O, Y is —CH$_2$—, A is carboxy, and B is horseradish peroxidase. Preferably, for the immunogen n=1, X is O, Y is —CH$_2$—, A is carboxy, and B is an accm optionally selected from the group consisting of bovine serum albumin, keyhole limpet haemocyanin, egg ovalbumin, and bovine thyroglobulin.

Optionally, there is provided a hapten having the general formula IA:

(IA)

wherein
R has the general structure (X)n-Y—Z;
and wherein
X is selected from the group consisting of N, O, or S; and n=0 or 1
Y is a substituted or unsubstituted $C_1$-$C_{10}$, more preferably a $C_1$-$C_6$, most preferably a $C_1$-$C_3$, branched or straight chain alkylene moiety; and
Z is selected from the group consisting of a carboxyl, dithiopyridyl, maleimidyl, amino, hydroxyl, thiol, and aldehyde moiety.

Optionally, the hapten has the general formula IA; wherein R is attached at the para position of the phenyl moiety; and has the general structure (X)n-Y—Z; wherein X is O; n=1; Y is an unsubstituted $C_1$ straight chain alkylene moiety; and Z is a carboxyl moiety.

Optionally, the hapten has the general formula IA; wherein R is attached at the para position of the phenyl moiety; and has the general structure (X)n-Y—Z; wherein X is O; n=1; Y is an unsubstituted $C_1$ straight chain alkylene moiety; and Z is an aldehyde moiety, optionally a homocysteine thiolactone aldehyde moiety.

Optionally, there is provided an immunogen having the general formula IB:

(IB)

wherein
R has the general structure (X)n-Y—Z;
and wherein
X is selected from the group consisting of N, O, or S; and n=0 or 1
Y is a substituted or unsubstituted $C_1$-$C_{10}$, more preferably a $C_1$-$C_6$, most preferably a $C_1$-$C_3$, branched or straight chain alkylene moiety; and
Z is selected from the group consisting of a carboxyl, dithiopyridyl, maleimidyl, amino, hydroxyl, thiol, and aldehyde moiety; and further comprises an antigenicity-conferring carrier material (accm) optionally selected from the group consisting of bovine serum albumin, keyhole limpet haemocyanin, egg ovalbumin, and bovine thyroglobulin.

Optionally, Z has the general structure -A-B, in which
A is selected from the group consisting of a carboxyl, dithiopyridyl, maleimidyl, amino, hydroxyl, thiol, and aldehyde moiety; and
B is an antigenicity-conferring carrier material (accm) optionally selected from the group consisting of bovine serum albumin, keyhole limpet haemocyanin, egg ovalbumin, and bovine thyroglobulin.

Optionally, the immunogen has the general formula IB; wherein R is attached at the para position of the phenyl moiety; and has the general structure (X)n-Y—Z; wherein X is O; n=1; Y is an unsubstituted C1 straight chain alkylene moiety; and Z is a carboxyl moiety; and further comprises an antigenicity-conferring carrier material (accm) selected from the group consisting of bovine serum albumin, keyhole limpet haemocyanin, egg ovalbumin, and bovine thyroglobulin.

Optionally, there is provided a detecting agent having the general formula IC:

(IC)

wherein
R has the general structure (X)n-Y—Z;
and wherein
X is selected from the group consisting of N, O, or S; and n=0 or 1
Y is a substituted or unsubstituted $C_1$-$C_{10}$, more preferably a $C_1$-$C_6$, most preferably a $C_1$-$C_3$, branched or straight chain alkylene moiety; and
Z is selected from the group consisting of a carboxyl, dithiopyridyl, maleimidyl, amino, hydroxyl, thiol, and aldehyde moiety; and further comprises a detecting label optionally selected from the group consisting of an enzyme, luminescent substance, and a radioactive label.

Optionally, Z has the general structure -A-B, in which
A is selected from the group consisting of a carboxyl, dithiopyridyl, maleimidyl, amino, hydroxyl, thiol, and aldehyde moiety; and
B is a detecting label selected from the group consisting of an enzyme, luminescent substance, and a radioactive label.

Optionally, the detecting agent has the general formula IC; wherein R is attached at the para position of the phenyl moiety; and has the general structure (X)n-Y—Z; wherein X is O; n=1; Y is an unsubstituted C1 straight chain alkylene moiety; and Z is a carboxyl moiety; and further comprises a detecting label enzyme, optionally horseradish peroxidase (HRP).

For the avoidance of doubt, the ring incorporating R is an aromatic benzene ring (phenyl moiety) which, in the context of Formula IA, would be named a meta- or para-substituted phenylene ring by the International Union of Pure and Applied Chemistry (IUPAC). Optionally, R is attached at the meta position of the phenyl moiety. Alternatively, R is attached at the para position of the phenyl moiety.

The immunogens are prepared by coupling a hapten (a pre-immunogenic molecule) to an accm by way of a crosslinker The accm and the crosslinkers are standard reagents in the field of antibody development. The accm comprises poly(amino acid) segments and is preferably bovine thyroglobulin. Crosslinkers are used to connect the hapten to the accm. An example of a crosslinker described herein is succinic anhydride, activated by N,N-dicyclohexylcarbodiimide and N-hydroxysuccinimide.

A second aspect of the invention is antibodies raised to the immunogens of the invention. The antibodies are further characterised by being able to bind to at least one structural epitope of a molecule comprising formula II:

wherein
R(a-R-b) is selected from the group consisting of and wherein
Q is any substituent other than H.

Optionally, Q is selected from the group consisting of HRP-C(O)—CH$_2$—O—, a hydroxyl moiety, and a methoxyl moiety.

The structural meaning of 'a molecule comprising formula II' implies that formula II incorporates a substituent—Q-(the substituent being an atom or group other than hydrogen) at either the meta or para position of the aromatic ring.

Preferably the molecule is:

wherein
Q is any substituent other than H.

Optionally, Q is selected from the group consisting of HRP-C(O)—CH$_2$—O—, a hydroxyl moiety, and a methoxyl moiety.

That Q can be both small substituents such as hydroxyl and methoxy or a macromolecular substituent such as HRP-C(O)—CH$_2$—O— attests to the ability of the antibodies of the invention to bind to diverse structures comprising the structural epitope depicted by formula II. The substituent Q is any atom or molecule including heteroatoms optionally attached to substituted and unsubstituted branched or straight chains, the chains also optionally comprising heteroatoms, carbocycles and heterocycles, the latter rings being optionally fused. Any of the aforementioned can be attached to macromolecules such as proteins.

The antibodies of the invention are obtained using standard methods. For example, immunogens of the invention are administered to a non-human mammalian host, preferably a sheep, to elicit antibody production after which harvested polyclonal or monoclonal antibodies are used to develop immunoassays. Other suitable immunoglobulin-derived molecules such as short-chain or single chain variable fragments are readily applied alternatives known to the skilled person. The antibodies of the invention have a high sensitivity towards venlafaxine and O-desmethylvenlafaxine. Preferably, the antibodies of the invention have an IC$_{50}$ value of about 18 ng/ml to venlafaxine. The limit of detection (LOD) and limit of quantification (LOQ) are two further measures of antibody sensitivity. The skilled person will recognise that the antibodies of the invention, having an IC$_{50}$ value of about 18 ng/ml to venlafaxine, will have a LOD and LOQ of much lower value.

Optionally, the at least one structural epitope comprises formula IV:

Also disclosed is a method of preparing an antibody capable of binding to venlafaxine and/or O-desmethylvenlafaxine; the method comprising the steps of administering an immunogen according to the present invention to a suitable host; and retrieving antibodies raised against the immunogen.

Further disclosed is a method of preparing an antibody capable of binding to at least one structural epitope of a molecule comprising formula II:

Wherein
R(a-R-b) is selected from the group consisting of and wherein
Q is any substituent other than H;
the method comprising the steps of administering an immunogen according to the present invention to a suitable host; and retrieving antibodies raised against the immunogen.

Optionally, is selected from the group consisting of HRP-C(O)—CH$_2$—O—, a hydroxyl moiety, and a methoxyl moiety.

Although the carbon of the aromatic ring with the non-explicit H-atom can have various substituents attached, these substituents, although influencing the relative degree of binding of the antibody to the epitope do not constitute the epitope to which the antibody binds, said epitope consisting of the cyclohexanol moiety, the ethyl tertiary amine moiety and the phenyl ring in the spatial configuration depicted by Formula II.

A further aspect of the invention is a method of detecting or determining venlafaxine and O-desmethylvenlafaxine in an in vitro sample or in a solution, the method comprising contacting the sample or solution with at least one detecting agent and at least one antibody of the invention; detecting or determining the detecting agent(s); and deducing from a calibration curve the presence of, or amount of, venlafaxine and O-desmethylvenlafaxine in the sample or solution. A further method of detecting or determining venlafaxine and O-desmethylvenlafaxine in an in vitro sample or in a solution comprises contacting the sample or solution with at least one detecting agent of the invention and at least one antibody that selectively binds to venlafaxine and O-desmethylvenlafaxine, detecting or determining the detecting agent(s) and deducing from a calibration curve the presence of, or amount of, venlafaxine and O-desmethylvenlafaxine in the sample or solution.

Optionally, the method is for detecting or determining both of venlafaxine and O-desmethylvenlafaxine in an in vitro sample or in a solution. Further optionally, the method is for simultaneously detecting or determining both of venlafaxine and O-desmethylvenlafaxine in an in vitro sample or in a solution.

Optionally or additionally, the method of detecting or determining venlafaxine and O-desmethylvenlafaxine in an in vitro sample or in a solution comprises contacting the sample or solution with at least one antibody capable of binding, optionally selectively binding, venlafaxine and O-desmethylvenlafaxine.

Optionally, the method of detecting or determining venlafaxine and O-desmethylvenlafaxine in an in vitro sample or in a solution comprises contacting the sample or solution with at least one detecting agent according to the present invention. Further optionally, the method of detecting or determining venlafaxine and O-desmethylvenlafaxine in an in vitro sample or in a solution comprises contacting the sample or solution with at least one detecting agent according to the present invention and at least one antibody capable of binding, optionally selectively binding, venlafaxine and O-desmethylvenlafaxine.

Optionally, the method of detecting or determining venlafaxine and O-desmethylvenlafaxine in an in vitro sample or in a solution comprises contacting the sample or solution with at least one hapten according to the present invention. Further optionally, the method of detecting or determining venlafaxine and O-desmethylvenlafaxine in an in vitro sample or in a solution comprises contacting the sample or solution with at least one hapten according to the present invention and at least one antibody capable of binding, optionally selectively binding, venlafaxine and O-desmethylvenlafaxine.

Optionally, the method of detecting or determining venlafaxine and O-desmethylvenlafaxine in an in vitro sample or in a solution comprises contacting the sample or solution with at least one antibody capable of binding, optionally selectively binding, venlafaxine and O-desmethylvenlafaxine. The antibody can be any antibody capable of binding, optionally selectively binding, venlafaxine and O-desmethylvenlafaxine. Optionally, the antibody is an antibody according to the present invention. Alternatively, the antibody is any other antibody capable of binding, optionally selectively binding, venlafaxine and O-desmethylvenlafaxine.

Optionally, the method of detecting or determining venlafaxine and O-desmethylvenlafaxine in an in vitro sample or in a solution comprises contacting the sample or solution with at least one compound comprising at least one structural epitope of a molecule comprising formula IV:

Optionally, the method comprises detecting or determining the detecting agent(s) and deducing from a calibration curve the presence of, or amount of, venlafaxine and O-desmethylvenlafaxine in the sample or solution relative to the calibration curve.

Optionally, the method comprises detecting or determining the hapten(s) and deducing from a calibration curve the presence of, or amount of, venlafaxine and O-desmethylvenlafaxine in the sample or solution relative to the calibration curve.

Optionally, the method comprises detecting or determining the antibody(ies) and deducing from a calibration curve the presence of, or amount of, venlafaxine and O-desmethylvenlafaxine in the sample or solution relative to the calibration curve.

The detecting agent comprises a suitable hapten, preferably the haptens disclosed herein, covalently bonded to a detectable labelling agent, the hapten moiety being able to bind to the antibodies of the invention. Preferably, the labelling agent is selected from the group consisting of an enzyme, a luminescent substance, a radioactive substance, and a mixture thereof. More preferably, the labelling agent is an enzyme, preferably a peroxidase, most preferably horseradish peroxidise (HRP). Detecting implies qualitatively analyzing for the presence or absence of a substance; determining means quantitatively analyzing the amount of substance. As the antibodies of the invention are able to bind venlafaxine and O-desmethylvenlafaxine, quantitative analysis will take the form of measuring the calibrator-equivalent amount. Any suitable in vitro biological sample may be used, but blood and urine are preferred.

Another aspect of the invention is a kit for detecting or determining venlafaxine and O-desmethylvenlafaxine, the kit comprising at least one antibody and/or at least one detecting agent of the invention. The kit may comprise one or more antibodies of the invention and one or more additional antibodies with different molecular specificities, i.e. these additional antibodies do not bind to the same structural epitopes as the antibodies of the invention. Such an arrangement enables a multiplexing approach to the detection or determination of drugs of abuse. The multiplexing approach preferably makes use of a planar substrate to which the antibodies are attached, such as a ceramic chip or an appropriately surface-modified glass slide. Beads may also be used.

A further aspect of the invention relates to an immunoassay for detecting or determining venlafaxine and O-desmethylvenlafaxine in an in vitro sample or in a solution, the immunoassay comprising an antibody capable of binding, optionally selectively binding, venlafaxine and O-desmethylvenlafaxine; and a compound comprising at least one structural epitope of a molecule comprising formula IV:

(IV)

Optionally, there is provided an immunoassay for detecting or determining venlafaxine and O-desmethylvenlafaxine in an in vitro sample or in a solution, the immunoassay comprising an antibody capable of binding, optionally selectively binding, venlafaxine and O-desmethylvenlafaxine; and a compound comprising at least one structural epitope of a molecule comprising formula II:

(II)

wherein
R(a-R-b) is selected from the group consisting of and wherein
Q is any substituent other than H.

Optionally, Q is selected from the group consisting of HRP-C(O)—CH$_2$—O—, a hydroxyl moiety, and a methoxyl moiety.

Optionally, the compound comprising at least one structural epitope of a molecule comprising formula IV further comprises a detecting label selected from the group consisting of an enzyme, luminescent substance, and a radioactive label.

Optionally, the immunoassay comprises an antibody capable of binding, optionally selectively binding, venlafaxine and O-desmethylvenlafaxine; and a compound comprising a detecting agent having the general formula IC:

(IC)

wherein
R has the general structure (X)n-Y—Z;
wherein
X is selected from the group consisting of N, O, or S; and n=0 or 1
Y is a substituted or unsubstituted $C_1$-$C_{10}$, more preferably a $C_1$-$C_6$, most preferably a $C_1$-$C_3$, branched or straight chain alkylene moiety; and
Z is selected from the group consisting of a carboxyl, dithiopyridyl, maleimidyl, amino, hydroxyl, thiol, and aldehyde moiety; and further comprises a detecting label optionally selected from the group consisting of an enzyme, luminescent substance, and a radioactive label.

Optionally, Z has the general structure-A-B, in which
A is selected from the group consisting of a carboxyl, dithiopyridyl, maleimidyl, amino, hydroxyl, thiol, and aldehyde moiety; and
B is a detecting label selected from the group consisting of an enzyme, luminescent substance, and a radioactive label.

Optionally, the detecting agent has the general formula IC; wherein R is attached at the para position of the phenyl moiety; and has the general structure (X)n-Y—Z; wherein X is O; n=1; Y is an unsubstituted $C_1$ straight chain alkylene moiety; and Z is a carboxyl moiety; and further comprises a detecting label enzyme, optionally horseradish peroxidase (HRP).

Optionally, the immunoassay comprises an antibody capable of binding, optionally selectively binding, venlafaxine and O-desmethylvenlafaxine; and a compound comprising a hapten having the general formula IA:

(IA)

wherein
R has the general structure (X)n-Y—Z;
wherein
X is selected from the group consisting of N, O, or S; and n=0 or 1
Y is a substituted or unsubstituted $C_1$-$C_{10}$, more preferably a $C_1$-$C_6$, most preferably a $C_1$-$C_3$, branched or straight chain alkylene moiety; and
Z is selected from the group consisting of a carboxyl, dithiopyridyl, maleimidyl, amino, hydroxyl, thiol, and aldehyde moiety.

Optionally, the hapten has the general formula IA; wherein R is attached at the para position of the phenyl moiety; and has the general structure (X)n-Y—Z; wherein X is O; n=1; Y is an unsubstituted $C_1$ straight chain alkylene moiety; and Z is a carboxyl moiety.

Optionally, the hapten has the general formula IA; wherein R is attached at the para position of the phenyl moiety; and has the general structure (X)n-Y—Z; wherein X is O; n=1; Y is an unsubstituted $C_1$ straight chain alkylene moiety; and Z is an aldehyde moiety, optionally a homocysteine thiolactone aldehyde moiety.

Optionally, the compound comprising the hapten further comprises a detecting label selected from the group consisting of an enzyme, luminescent substance, and a radioactive label.

Also disclosed is a kit for detecting or determining venlafaxine and O-desmethylvenlafaxine in an in vitro sample or in a solution; the kit comprising at least one antibody capable of binding, optionally selectively binding, venlafaxine and O-desmethylvenlafaxine; and means for detecting or determining the antibody(ies) and deducing from a calibration curve the presence of, or amount of, venlafaxine and O-desmethylvenlafaxine in the sample or solution relative to the calibration curve. The kit can optionally further comprise a detecting label selected from the group consisting of an enzyme, luminescent substance, and a radioactive label or at least one antibody comprising a detecting label selected from the group consisting of an enzyme, luminescent substance, and a radioactive label. The kit can comprise first and second antibodies, each antibody capable of binding, optionally selectively binding, venlafaxine and O-desmethylvenlafaxine. Either or both of the first and second antibody can further comprise a detecting label selected from the group consisting of an enzyme, luminescent substance, and a radioactive label.

The kit can optionally comprise at least one detecting agent according to the invention; and means for detecting or determining the detecting agent(s) and deducing from a calibration curve the presence of, or amount of, venlafaxine and O-desmethylvenlafaxine in the sample or solution relative to the calibration curve.

The kit can optionally comprise at least one hapten according to the invention; and means for detecting or determining the hapten(s) and deducing from a calibration curve the presence of, or amount of, venlafaxine and O-desmethylvenlafaxine in the sample or solution relative to the calibration curve. The kit can optionally further comprise a detecting label selected from the group consisting of an enzyme, luminescent substance, and a radioactive label or at least one hapten comprising a detecting label selected from the group consisting of an enzyme, luminescent substance, and a radioactive label.

EXAMPLES

Example 1

Preparation of Haptens, Immunogens and Detecting Agents

Although haptens provide defined structural epitopes, they are not in themselves immunogenic and therefore need to be conjugated to an antigenicity conferring carrier material (accm) which will elicit an immunogenic response when administered to a host animal. Appropriate accms commonly contain poly(amino acid) segments and include polypeptides, proteins and protein fragments. Illustrative examples of useful accms are bovine serum albumin (BSA), egg ovalbumin, bovine gamma globulin, BTG, keyhole limpet haemocyanin (KLH) etc. Alternatively, synthetic poly (amino acids) having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen.

The haptens can also be coupled to a detectable labelling agent such as an enzyme, a luminescent compound or a radioactive label for the preparation of detecting agents for use in the immunoassays. The luminescent compound may be a fluorescent substance, for example, a monovalent residue of fluorescein or a derivative thereof. Immunogen formation for the invention described herein involves conventional conjugation chemistry. It is known in the art that stronger immunogenic responses to the immunogen are achieved when several haptens are conjugated to the accm. In order to confirm that adequate conjugation of hapten to accm has been achieved, prior to immunisation, each immunogen is evaluated using matrix-assisted UV laser desorption/ionisation time-of-flight mass spectroscopy (MALDI-TOF MS). A minimum conjugation of 6 molecules of hapten per accm is preferred.

A. General Procedure for MALDI-TOF Analysis of Immunogens.

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 µl) were analysed using a matrix of sinapinic acid and bovine serum albumin (Fluka) was used as an external calibrant.

B. Preparation of Antisera

In order to generate polyclonal antisera, an immunogen of the present invention is mixed with Freund's adjuvant and the mixture is injected into a host animal, such as rabbit, sheep, mouse, guinea pig or horse. Sheep are the preferred host animal. Further injections (boosts) are made and serum is sampled for evaluation of the antibody titer. When the optimal titer has been attained, the host animal is bled to yield a suitable volume of specific antiserum. The degree of antibody purification required depends on the intended application. For many purposes, there is no requirement for purification, however, in other cases, such as where the antibody is to be immobilised on a solid support, purification steps can be taken to remove undesired material and eliminate non-specific binding.

C. Immunoassay Development

The process of developing an immunoassay is well known to the person skilled in the art. Briefly, for a competitive immunoassay in which the target analyte is a non-immunogenic molecule such as a hapten, the following process is conducted: antibodies are produced by immunising an animal, preferably a mammalian animal, by repeated administration of an immunogen. The serum from the immunised animal is collected when the antibody titer is sufficiently high. A detecting agent is added to a sample containing the target analyte and the raised antibodies, and the detecting agent and analyte compete for binding to the antibodies. The detecting agent is a compound capable of binding with the antibodies of the invention and which is detectable, thus enabling the qualitative or quantitative assay. It can be, for example, an enzyme, a luminescent material or a radioactive species. It is preferably HRP. Sometimes additional compounds must be added to enable detection. For example, when the enzyme HRP is used as the detecting agent, hydrogen peroxide and luminol are added to sample mixture to enable visualization. The process may comprise fixing said serum antibodies to a backing substrate such as a polystyrene solid support or a ceramic chip. The antibodies can be polyclonal or monoclonal using standard techniques. The signal emitted in the immunoassay is proportionate to the amount of detecting agent bound to the antibodies which in turn is inversely proportionate to the analyte concentration. The signal can be detected or quantified by comparison with a calibrator.

Example 2

Preparation of 4-Methoxy-N,N-Dimethylbenzene Acetamide 2

4-Methoxyphenylacetic acid 1 (20 g, 0.12 mol) was dissolved in thionyl chloride (100 ml) and the mixture was heated at reflux for 2 hours. The mixture was then cooled to room temperature and evaporated to dryness. The residue obtained was dissolved in dichloromethane (200 ml) and treated with an excess of gaseous dimethylamine. The mixture was stirred overnight at room temperature and the solvent evaporated. The residue was dissolved in dichloromethane (250 ml) and the solution washed with saturated sodium bicarbonate solution (100 ml), 1M hydrochloric solution (100 ml), water (100 ml), brine (100 ml), dried over sodium sulfate and evaporated to give 18.5 g (80%) of the 4-methoxy-N, N-dimethylbenzene acetamide 2.

Example 3

Preparation 1-[(4-methoxy)[(dimethylamino)carbonyl]methyl]cyclohexanol 3

4-Methoxy-N,N-dimethylbenzene acetamide 2 (9.65 g, 0.05 mol) was dissolved in anhydrous THF (160 ml) and the solution cooled to −78° C. under nitrogen. n-Butyllithium (1.6 M) in hexane (31.5 ml, 0.05 mol) was added dropwise, the temperature being maintained below −70° C. An orange coloured precipitate formed. After the addition, the reaction mixture was stirred for 20 minutes at −78° C. and cyclohexanone (6 ml, 0.058 mol) was added, and the mixture was stirred again at the same temperature for 1 hour. The reaction mixture was poured into saturated ammonium chloride solution (400 ml) and stirred for 10 minutes. The layers were separated and the aqueous layer extracted with diethyl ether (2×150 ml). The combined organic solution was washed with water (100 ml), brine (100 ml), dried over sodium sulfate, filtered and concentrated to dryness. Recrystallisation of the crude product from isopropanol give the 1-[(4-methoxy)[(dimethylamino)carbonyl]methyl]cyclohexanol 3 as a white solid 6.11 g (42.0%).

Example 4

Preparation of (RS)-1-[2-(dimethylamino)-1-(4-methoxyphenyl)ethyl]cyclohexanol (venlafaxine) 4

To a cooled (0° C.) suspension of lithium aluminium hydride 1.6M in tetrahydrofuran (11.5 ml, 0.023 mol) in THF (20 ml) was added concentrated sulphuric acid (0.7 ml) and the mixture was stirred for 1 hour at 0° C. To this cooled mixture was added rapidly a solution of 1-[(4-methoxy)[(dimethylamino)carbonyl]methyl]cyclohexanol 3 (5 g, 0.017 ml) in THF (40 ml). The reaction mixture was stirred for 1 hour at 0° C. A THF-water mixture (1:1 v/v 7.5 ml) was added slowly followed by 10% sodium hydroxide solution (12.5 ml). The mixture was filtered and the residue obtained washed by ethyl acetate. The combined filtrate was dried over sodium sulfate. The addition of diethyl ether to residue gave a yellow solid which was washed by ether, filtered and dried to give 1.5 g (32%) of venlafaxine 4.

Example 5

Preparation of (RS)-1-[2-(dimethylamino)-1-(4-hydroxyphenyl)ethyl]cyclohexanol (O-desmethyl-venlafaxine) 5

A slurry solution of sodium sulfide (3.6 g, 4.6 mmol) in 1-methylpyrrolidone (12.0 ml) was heated at 150° C. for 30 minutes. To the resulting solution was added a solution of venlafaxine 4 (4.22 g, 13.44 mmol) in 1-methylpyrrolidone (20 ml) in one portion and the reaction mixture was stirred at 145° C. for 24 hours then at room temperature for two days. The reaction mixture was poured into water (150 ml) and extracted with ethyl acetate (200 ml). After cooling the ethyl acetate at 0° C. the O-desmethylvenlafaxine 5 was recrystallized. The crystals obtained were filtered, washed by ethyl acetate and dried under vacuum to give 1.86 g (52%) of the title compound.

Example 6

Preparation of O-(tert-butoxymethylether)-O-desmethylvenlafaxine 6

To a suspension of potassium carbonate (1.93 g, 13.96 mmol) in a mixture of DMF (30 ml) and acetonitrile (20 ml) under nitrogen was added O-desmethylvenlafaxine 5 (1.6 g, 6.1 mmol) and the mixture was stirred at room temperature for 30 minutes. To this suspension was added tert-butyl bromoacetate (1.3 ml, 9.1 mmol) and the mixture was heated at reflux for 1.5 hours. The solution was then cooled to RT and the solvents were removed under vacuum. Water (100 ml) was added and the solution was extracted several times with dichloromethane. The combined dichloromethane solution was washed by brine (100 ml), dried over sodium sulphate filtered and concentrated to dryness to give 2.5 g (100%) of yellow powder showing only a single spot by TLC of the title compound O-(tert-butoxymethylether)-O-desmethylvenlafaxine 6.

Example 7

Preparation of O-(carboxymethylether)-O-desmethylvenlafaxine 7 (Hapten-1)

To a solution of the ester 6 (2.26 g, 6 mmol) in dichloromethane (50 ml) was added trifluoroacetic acid (TFA) (10 ml) and the mixture was stirred at RT for 1.5 hours. The solution was concentrated to dryness and the crude product obtained was triturated with ether to give a yellow hydroscopic solid of 7 (Hapten-1) as TFA salt (1.72 g, 68%).

Example 8

Conjugation of Hapten-1 to BSA (Immunogen-I)

To a solution of O-(carboxymethylether)-O-desmethylvenlafaxine 7 (Hapten-1) (48.3 mg, 0.115 mM) in DMF (2 ml) was added N-hydroxysuccinimide (415 µl) DMF solution (50 mg/ml) and EDC hydrochloride (1.730 ml) DMF solution (20 mg/ml) and the mixture was incubated on the roller for 2 hours at RT. The solution was added dropwise to a solution of BSA (200 mg, 2.3 µmol) in 50 mM phosphate buffer (pH 8) (10 ml). The mixture was then stirred overnight at 4° C. The solution was then dialysed against 50 mM phosphate buffer pH 7.2 (3 changes) for 24 hours at 4° C., and freeze-dried. MALDI results showed 9.02 molecules of Hapten-1 had been conjugated to one molecule of BSA.

Example 9

Conjugation of Hapten-1 to BTG (Immunogen-II)

To a solution of O-(carboxymethylether)-O-desmethylvenlafaxine 7 (Hapten-1) (48.3 mg, 0.115 mM) in DMF (2 ml) was added N-hydroxysuccinimide (415 µl) DMF solution (50 mg/ml) and EDC hydrochloride (1.73 ml) DMF solution (20 mg/ml) and the mixture was incubated on the roller for 2 hours at room temperature. The solution was added dropwise to a solution of BTG (150 mg, 2.3 µmol) in 50 mM phosphate buffer (pH 8) (10 ml). The mixture was then stirred overnight at 4° C. The solution was then dialysed against 50 mM phosphate buffer pH 7.2 (3 changes) for 24 hours at 4° C., and freeze-dried.

Example 10

Conjugation of Hapten-1 to HRP

EDC hydrochloride (10 mg) was dissolved in water (0.5 ml) and immediately added to a solution of O-(carboxymethylether)-O-desmethylvenlafaxine 7 (Hapten-1) (2 mg) in DMF (0.2 ml). After mixing, this solution was added dropwise to a solution of HRP (20 mg) in water (1 ml). Sulfo-NHS (5 mg) was added and the reaction mixture was incubated in the dark at RT overnight. Excess hapten was removed with double PD-10 columns (Pharmacia) in series, pre-equilibrated with PBS at pH 7.2. The hapten-HRP conjugate was then dialysed overnight against 10 L of PBS at pH 7.2 at 4° C.

Example 11

Preparation of O-(carboxymethylether homocysteine thiolactone)-O-desmethylvenlafaxine 8 (Hapten-2)

To a solution of O-(carboxymethylether)-O-desmethylvenlafaxine 7 (Hapten-1) (200 mg, 0.478 mmol) in pyridine (5 ml) were added homocysteine thiolactone hydrochloride (128.6 mg, 0.836 mmol) and EDC hydrochloride (160.4 mg, 0.836 mmol) and the mixture stirred at RT overnight. Evaporation of the solvent under high vacuum, and the crude mixture obtained was purified by chromatography on silica gel using methanol/chloroform (1:9) to give the title compound (Hapten-2) (198 mg, 98%) as a brown oil.

Example 12

Immunoassay of venlafaxine and O-desmethylvenlafaxine

A semi-automated Evidence Investigator analyser (Randox Laboratories Ltd., Crumlin, UK) was used as the platform for a biochip assay for the detection of venlafaxine and O-desmethylvenlafaxine. Immunogen II was administered to adult sheep on a monthly basis to provide target-specific polyclonal antisera. IgG was extracted from the antisera, and the purified antibody was immobilised on a biochip (9 mm×9 mm). The assay is based on competition for binding sites of a polyclonal antibody between Hapten-1HRP detecting agent (Example 10) and venlafaxine and O-desmethylvenlafaxine and potential cross-reactants. The antibody was immobilised and stabilised onto the biochip surface as previously described (Fitzgerald et al., 2005). Assay diluent (155 µL), calibrator/venlafaxine and O-desmethylvenlafaxine or potential cross-reactant (25 µL) followed by Hapten-1 HRP detecting agent (120 µL) were added to the appropriate biochip. The biochips were then incubated for 30 minutes at 30° C. on a thermoshaker set at 370 rpm. The biochips were then subjected to 2 quick wash cycles using the wash buffer provided, followed by 4×2 minute wash cycles. 250 µL of signal (1:1 luminol+peroxide, v/v) was then added to each biochip, and after 2 minutes the biochip carrier was imaged in the Evidence Investigator analyser. Calibration curves were generated and these were used to determine the sensitivity and specificity of the immunoassay for venlafaxine, O-desmethylvenlafaxine and potential cross-reactants. The results of this study are presented in Table 1, cross-reactivity being calculated according to the following formula:

$$\%CR = IC_{50}, \text{O-desmethylvenlafaxine}/IC_{50}, CR \times 100$$

where % CR is the percentage cross-reactivity, IC50, O-desmethylvenlafaxine is the concentration of O-desmethylvenlafaxine which causes 50% displacement of signal and IC50, CR is the concentration of venlafaxine or potential cross-reactant that causes 50% displacement of signal.

Chemicals

Chemicals were sourced from Sigma-Aldrich-Fluka.

TABLE 1

Results

| Standard | IC$_{50}$ (ng/ml) | % Cross-reactivity |
|---|---|---|
| Venlafaxine | 18.31 | 100 |
| O-Desmethylvenlafaxine | 37.86 | 48.4 |
| Tramadol | >320 | <5.7 |
| N-Desmethyltramadol | >320 | <5.7 |
| O-Desmethyltramadol | >320 | <5.7 |
| Meperidine | >320 | <5.7 |
| Methylphenidate | >320 | <5.7 |
| PCP | >320 | <5.7 |

The cross-reactivity data highlights the selectivity of the antibodies of the invention for venlafaxine and O-desmethylvenlafaxine. The cross-reactivity data also highlight the selectivity of the antibodies of the invention for the epitope of Formula IV, which is shared by venlafaxine and O-desmethylvenlafaxine, but is not shared by any of the other analytes tested; each of which demonstrated less than 5.7% cross-reactivity. The IC$_{50}$ data for each of venlafaxine and O-desmethylvenlafaxine (18.31 ng/ml and 37.86 ng/ml, respectively) show that the antibodies of the invention can be used for detecting or determining either venlafaxine or O-desmethylvenlafaxine in an in vitro sample or in a solution; and/or can be used for detecting or determining the sum of venlafaxine and O-desmethylvenlafaxine in an in vitro sample or in a solution.

What is claimed is:

1. A method of detecting or determining venlafaxine and O-desmethylvenlafaxine in an in vitro sample or in a solution, the method comprising:

(a) contacting the sample or solution with at least one polyclonal antibody having a cross-reactivity of about 100% for venlafaxine, about 48.4% for O-desmethylvenlafaxine, and about <5.7% for tramadol, N-desmethyltramadol, O-desmethyltramadol, mepridine, methylphenidate, and phencyclidine (PCP);

(b) contacting the sample or solution with at least one detecting agent, wherein said at least one detecting agent is a compound formula 7:

attached through its carboxyl group to horse radish peroxidase (HRP);

(c) allowing said at least one polyclonal antibody to bind said at least one detecting agent, venlafaxine, and O-desmethylvenlafaxine; and (d) deducing from a calibration curve the presence of, or amount of, venlafaxine and O-desmethylvenlafaxine in the sample or solution relative to the calibration curve of the presence of, or amount of, said at least one detecting agent.

* * * * *